(12) United States Patent
Mollenhauer et al.

(10) Patent No.: US 9,828,636 B2
(45) Date of Patent: Nov. 28, 2017

(54) IN VITRO METHOD OF PREDICTIVE ASSESSMENT OF THE PROSPECTS OF SUCCESS OF AN IMPLANT AND/OR TRANSPLANT

(71) Applicant: TETEC Tissue Engineering Technologies AG, Reutlingen (DE)

(72) Inventors: Jürgen Mollenhauer, Reutlingen (DE); Christoph Gaissmaier, Reutlingen (DE); Karin Benz, Göppingen (DE)

(73) Assignee: TETEC Tissue Engineering Technologies AG, Reutlingen (DE)

( * ) Notice: Subject to any disclaimer, the term of this patent is extended or adjusted under 35 U.S.C. 154(b) by 0 days.

(21) Appl. No.: 14/779,639

(22) PCT Filed: Mar. 20, 2014

(86) PCT No.: PCT/EP2014/055667
§ 371 (c)(1),
(2) Date: Sep. 24, 2015

(87) PCT Pub. No.: WO2014/154569
PCT Pub. Date: Oct. 2, 2014

(65) Prior Publication Data
US 2016/0046989 A1 Feb. 18, 2016

(30) Foreign Application Priority Data

Mar. 27, 2013 (DE) .................. 10 2013 205 516
Jan. 28, 2014 (DE) .................. 10 2014 201 528

(51) Int. Cl.
*C12Q 1/68* (2006.01)

(52) U.S. Cl.
CPC ......... *C12Q 1/6881* (2013.01); *C12Q 1/6883* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 9,080,213 B2   7/2015 Mollenhauer et al.

FOREIGN PATENT DOCUMENTS

| DE | 102 43 131 | 4/2004 | |
|---|---|---|---|
| DE | 10 2010 033 565 | 2/2012 | |
| EP | 1 824 420 | 8/2007 | |
| WO | 2006/045330 | 5/2006 | |
| WO | 2011/127561 | 10/2011 | |
| WO | WO 2012013712 A1 * | 2/2012 | ......... G01N 33/5005 |

OTHER PUBLICATIONS

Satija, N.K. et al., "High Throughput Transcriptome Profiling of Lithium Stimulated Human Mesenchymal Stem Cells Reveals Priming towards Osteoblastic Lineage," *PLOS ONE*, Jan. 2013, vol. 8, issue 1, pp. 1-12.
Mas, V. et al., "Transcriptome at the Time of Hepatitis C Virus Recurrence May Predict the Severity of Fibrosis Progression after Liver Transplantation," *Liver Transplantation*, 2011, vol. 17, pp. 824-835.
Ameling, S. et al., "Myocardial Gene Expression Profiles and Cardiodepressant Autoantibodies Predict Response of Patients with Dilated Cardiomyopathy to Immunoadsorption Therapy," *European Heart Journal*, 2013, vol. 34, pp. 666-675.
Bernstein, P. et al., "Expression Pattern Differences between Osteoarthritic Chondrocytes and Mesenchymal Stem Cells during Chondrogenic Differentiation," *Osteoarthritis and Cartilage*, 2010, vol. 18, pp. 1596-1607.
Barlic, A. et al., "Quantitative Analysis of Gene Expression in Human Articular Chondrocytes Assigned for Autologous Implantation," *Journal of Orthopaedic Research*, Jun. 2008, pp. 847-853.
Cameron, T.L. et al., "Global Comparative Transcriptome Analysis of Cartilage Formation in vivo," *BMC Developmental Biology*, 2009, vol. 9, No. 20, 17 pages.
Ashwell, M.S. et al., "Gene Expression Profiling of Chondrocytes from a Porcine Impact Injury Model," *Osteoarthritis and Cartilage*, 2008, vol. 16, pp. 936-946.
Agarwal, S. et al., "Transcriptome-Wide Analysis of Articular Chondrocytes Exposed to Biomechanical Forces of Various Magnitudes," *Poster Presentations—Cartilage/Chondrocyte Biology*, Sep. 2008, vol. 16, Supplement 4, pp. S111-S112.
Karlson, C. et al., "Genome-Wide Expression Profiling Reveals New Candidate Genes Associated with Osteoarthritis," *Osteoarthritis Cartilage*, Apr. 2010, vol. 18, No. 4, pp. 581-592 (Abstract only).

* cited by examiner

*Primary Examiner* — Antonio Galisteo Gonzalez
(74) *Attorney, Agent, or Firm* — Lewis Kohn & Walker LLP; David M. Kohn (57) ABSTRACT

An in vitro method of prognostically assessing tissue regeneration capacity and/or cellular potency and/or the prospects of success of an implantation and/or transplantation, wherein the transcriptome and/or the gene expression of cells, the gene expression originating from the transcriptome, are analyzed.

7 Claims, 6 Drawing Sheets

IN VITRO METHOD OF PREDICTIVE ASSESSMENT OF THE PROSPECTS OF SUCCESS OF AN IMPLANT AND/OR TRANSPLANT

TECHNICAL FIELD

This disclosure relates to an in vitro method of prognostically assessing tissue regeneration capacity and/or cellular potency and/or the prospects of success of an implantation and/or transplantation.

BACKGROUND

The creation of gene expression profiles or the analysis of the transcriptome has, with the establishment of microarray technology, taken hold to become an important tool in biomedical science.

Particularly the development of second-generation RNA sequencing methods (next-generation sequencing, NGS) has not only resulted in a drastic lowering of the costs for carrying out a transcriptome analysis, but has also increased the accuracy in identifying hitherto unknown gene activities. Examples of application areas of gene expression profiles are the diagnosis and prognosis of diseases, the aftercare analysis of therapies, the analysis of genetic predispositions, the investigation of pharmacological mechanisms of action and also the qualitative and quantitative investigation of growth and differentiation processes of cells and tissues.

A customary method of evaluating gene expression data is differential analysis, by means of which both the expression of known genes is investigated and the detection of unknown genes can be carried out. In that method, the expression data of the sample to be investigated are aligned or compared with the gene expression pattern of reference samples or else with the expression data of selected genes. For example, when investigating the expression of pathophysiologically relevant genes, the expression data of healthy tissue (reference sample) are compared with the expression data of diseased tissue (measurement sample) such as tumor tissue, for example. On the basis of this comparison, information can be provided in relation to the qualitative (yes/no answer) or the quantitative expression (increase or decrease in expression) of selected genes and this in turn can be assigned to a particular state, for example, a pathological state.

DE 10 2010 033 565 A1 discloses various markers for the in vitro determination of the pharmaceutical identity, purity or potency of chondrocytes (cartilage cells), by which the chondrocytes can be tested for their suitability for an expectedly successful chondrocyte transplantation. The establishment of said markers was borne by the fact that chondrocytes can vary greatly with respect to their suitability for use as autologous cells for an implantation for cartilage regeneration, specifically not only chondrocytes from one donor in relation to chondrocytes from another donor, but also chondrocytes from the same donor. Furthermore, it was taken into account that the culturing of chondrocytes can alter their properties such that they are no longer as suitable for an implantation as directly after isolation from the donor.

Although a selective analysis of a few genes, especially those involved in cellular metabolism, can definitely lead to powerful results in the quality assurance of cells to be transplanted, the results of such an approach are nevertheless limited in their statistical meaningfulness, especially since chondrocyte differentiation is merely one parameter for assessing cure-related success.

SUMMARY

We provide an in vitro method of prognostically assessing tissue regeneration capacity and/or cellular potency and/or prospects of success of an implantation and/or transplantation, including analysing a transcriptome and/or gene expression of cells, said gene expression originating from the transcriptome.

BRIEF DESCRIPTION OF THE DRAWINGS

FIG. 1A shows expression values of GAPDH determined by means of qRT-PCR (quantitative real-time PCR). For each gene, the box plot shows the 25%-75% range (gray box), the 5%/95% range (horizontal lines above and below the box), the median (line within the box) and also outliers (black dots). The GAPDH expression values were standardized to the total mRNA expression in 3 repetitive measurements (each using the entire 422 patient samples). The differences between the three datasets are not statistically significant (simple ANOVA), indicating the reliability of the qRT-PCR method.

FIG. 1B shows expression values of six selected marker genes determined by means of qRT-PCR (quantitative real-time PCR). For each gene, the box plot shows the 25%-75% range (gray box), the 5%/95% range (horizontal lines above and below the box), the median (line within the box) and also outliers (black dots). The expression of the six marker genes is shown as a negative dCt value in relation to GAPDH. The data were gathered as part of a routine quality control at the time of harvesting of the monolayer cell cultures directly before the colonization of the support (NOVOCART® Basic). The mRNA expression value obtained for each patient was standardized to the cDNA standard of the patient in question (according to the information from the manufacturer concerning the cDNA synthesis kit), and so a direct comparability of the expression data for each of the six selected genes is ensured. COL1: COL1A2, collagen type I alpha-2 chain; COL2: COL2A1, collagen type III) alpha-1 chain; AGG: ACAN, aggrecan; IL1: IL1-$\beta$, interleukin-1$\beta$; BSP2: bone sialoprotein 2; FLT-1: vascular endothelial growth factor receptor 1.

FIG. 2 shows the distribution of the expression levels of different protein families in cultured human chondrocytes. The RPKM expression values shown on a logarithmic scale were gathered for each of the 20 samples as part of a transcriptome analysis. For each gene, the box plot shows a 25%-75% range (gray box), the median (line within the box) and also the entire range (horizontal lines above and below the box). Triangles label genes to which positive (e.g., FGF-2) or anabolic properties (e.g., ACAN) with respect to cartilage can be assigned. Diamonds label genes to which undesired (e.g., collagen I) or negative or catabolic properties (e.g., interleukin-1, ADAM-TS5) are attributed. Gene designations correspond to the NCBI nomenclature.

FIG. 5 shows the hierarchical clustering on the basis of the genomewide expression data of the 20 samples (S1 to S20). The clustering is based on a Pearson correlation between the expression values of all the genes of a sample using the neighbour joining algorithm. The samples are referred to as "positive" or "negative" according to the clinical result of the implantation in the patients in question. While the variance among the negative samples is considerably higher than among the positive samples, a clear separation between the underlying clinical results can be registered. This separation indicates that the clinical results—transplantation which proceeded positively or negatively—can be assigned to a transcriptome phenotype of the cells used for the implantation.

DETAILED DESCRIPTION

Against this background, we provide a method which circumvents known shortcomings and allows in particular more valid individual prognostics.

We provide an in vitro method of prognostically assessing or prognosing tissue regeneration capacity and/or cellular potency and/or the prospects of success of an implantation, preferably cell implantation, and/or transplantation, more particularly prognostically assessing or prognosing a failure of implantation and/or transplantation.

The method is particularly notable for the fact that the transcriptome of cells, more particularly cells from a patient (patient cells), and/or the gene expression of cells, more particularly cells from a patient (patient cells), the gene expression originating from the transcriptome or being based on the transcriptome, are/is analyzed in vitro.

In the transcriptome analysis and/or the analysis of a gene expression based on the transcriptome, it is especially advantageously possible to capture the transcription and/or translation behavior of all the genes of a cell and not only the transcription or translation of a few genes, especially those specifically selected on the basis of their significance for cellular metabolism. The transcriptome analysis makes it possible to create in particular a complete metabolic profile, expressed in the gene expression activity of the cells in question, preferably patient cells.

We found that, surprisingly, the transcriptome and/or gene expression profiles obtained as part of the transcriptome analysis of patient cells can be assigned a therapeutic significance in terms of the tissue regeneration capacity and the prospects of success of an implantation- and/or transplantation-related measure in the patient(s) in question. It was possible for the inventors to successfully verify this as part of a retrospective clinical follow-up using the example of a matrix- or support-assisted autologous chondrocyte transplantation (MACT).

Since the profiles obtained are based on an in vitro analysis of the transcriptome and/or on a gene expression based on the transcriptome, individual prognostics which is more valid compared to generic methods, i.e., individual prognostics with greater statistical meaningfulness, is possible.

In other words, we therefore provide a method of prognosticating tissue regeneration, cellular potency, a success or failure of implantation and/or a success or failure of transplantation.

As used herein, the expression "cell implantation" relates to an implantation using an implant loaded or inoculated with cells.

As used herein, the expression "transcriptome" encompasses at least the sum total of the genes transcribed from DNA to mRNA (messenger RNA) in a cell at a particular time point. However, the expression "transcriptome" preferably encompasses the sum total of the genes transcribed from DNA to RNA in a cell at a particular time point, i.e., the entirety of all RNA molecules produced in a cell.

As used herein, the expression "transcriptome profile" (or transcriptome pattern) denotes the profile (or pattern) of all the transcripts of cells that are preferably capturable by means of hybridization-based and/or sequence-based methods, more particularly second-generation sequencing methods.

As used herein, the expression "gene expression" encompasses the synthesis of RNA, more particularly mRNA (primary gene product), regulatory RNA and/or further RNA types, that takes place over the course of transcription and/or the translation to proteins (secondary gene products) that is based on mature mRNA sequences. Examples of regulatory RNA include microRNA (miRNA), small interfering RNA (siRNA) and/or small nuclear RNA. Examples of the further RNA types additionally mentioned in this paragraph are ribosomal RNA (rRNA) and/or transfer RNA (tRNA), which are likewise counted among the primary gene products.

As used herein, the expression "gene expression profile" (or gene expression pattern) denotes the interpretation of the data preferably generated by means of hybridization-based and/or sequence-based methods, more particularly second-generation sequencing methods, as a profile (or pattern) of the gene activities of the cells investigated.

As used herein, the expression "tissue regeneration" can fundamentally encompass the regeneration of any body tissue or patient tissue. However, the expression "tissue regeneration" preferably encompasses the regeneration of supporting tissue, preferably regeneration of cartilage tissue, particularly preferably regeneration of articular cartilage, and/or regeneration of intervertebral disk tissue.

Accordingly, the expression "tissue regeneration capacity" can fundamentally encompass the capacity for regenerating any body tissue or patient tissue, more particularly the capacity for regenerating supporting tissue, preferably for regenerating cartilage tissue, particularly preferably for regenerating articular cartilage, and/or for regenerating intervertebral disk tissue.

As used herein, the expression "cellular potency" is to be understood to mean the capacity of tissue cells to develop tissue-specific properties and/or to maintain or resume the development of tissue-specific properties, especially after a preceding in vitro culturing. For example, the potency of chondrocytes is to be understood to mean their capacity to produce extracellular matrix and/or to resume the production of extracellular matrix, especially when the chondrocytes are implanted into a defective site to be treated.

As used herein, the expression "matrix- or support-assisted cell implantation" or "matrix- or support-assisted cell transplantation" means the implantation or transplantation of an implant provided or inoculated with autologous cells.

The cells can fundamentally be of human and/or animal origin. In other words, the cells can be human and/or animal cells.

Preferably, the cells originate from a human patient.

More particularly, the cells can be endogenous or autologous cells.

Preferably, the cells are extracted from a patient in the form of a tissue sample. Depending on the nature or origin of the sample, it may be advantageous to process the sample before carrying out the transcriptome analysis. A suitable processing of the sample can comprise steps such as centrifugation, concentration, homogenization, in vitro multiplication and also further processing steps fundamentally known to a person skilled in the art.

Preferably, the cells originate from a patient tissue, the regeneration capacity of which and/or the cellular potency of which is to be assessed.

More particularly, the cells originate from a patient tissue having a defect which is to be treated by means of the implantation and/or transplantation.

Preferably, the cells originate from a supporting tissue, more preferably cartilage tissue, particularly preferably articular cartilage tissue, and/or intervertebral disk tissue.

In a further example, the cells are supporting tissue cells, preferably chondrocytes (cartilage cells), and/or precursor cells thereof, particularly preferably articular chondrocytes, intervertebral disk cells, more particularly nucleus cells and/or annulus cells, and/or precursor cells thereof.

In a further example, the cells are healthy cells or cells originating from healthy tissue parts or areas.

Particularly preferably, the implantation is a matrix- or support-assisted autologous cell implantation, preferably matrix- or support-assisted autologous chondrocyte implantation (MACI). Suitable matrices are, in particular, collagen supports. A preferred matrix or a preferred collagen support is a multilayered implant composed of a pericardium membrane and a collagen sponge, the collagen sponge preferably having column-shaped pores which are oriented perpendicularly or substantially perpendicularly in relation to the pericardium membrane and can be formed by means of one-sided lyophilization. Such a collagen support is commercially sold by the applicant, for example under the name NOVOCART® Basic or NOVOCART® 3D. With regard to further features and advantages of such a collagen support, reference is additionally made to EP 1 824 420 B1, the disclosure content of which with respect to the implant described therein relating to the repair of a cartilage defect is hereby incorporated in the present description by express reference.

In a further example, the transplantation is an autologous cell transplantation, preferably autologous chondrocyte transplantation.

Preferably, the cells are cultured and, in particular, multiplied in vitro before carrying out the transcriptome analysis and/or the analysis of the gene expression originating from the transcriptome. The culturing can, for example, take place in a culture medium which is preferably enriched with autologous or homologous serum.

The cells can, in particular, be cultured over a period of from 14 days to 30 days, more particularly from 17 days to 24 days, preferably from 19 days to 21 days.

Preferably, the prognostic assessment is performed on the basis of a transcriptome profile obtained by means of the transcriptome analysis and/or a gene expression profile originating from the transcriptome profile.

In a further example, the transcriptome profile and/or the gene expression profile originating from the transcriptome profile are/is compared with a transcriptome profile and/or gene expression profile of the same cell type, the latter profile(s) being indicative of, or specific for, or characteristic of, a successful tissue regeneration, successful implantation and/or successful transplantation and/or the presence of cellular potency.

As an alternative or as a supplement to the preceding example, the transcriptome profile and/or the gene expression profile originating from the transcriptome profile are/is compared with a transcriptome profile and/or gene expression profile of the same cell type, the latter profile(s) being indicative of, or specific for, or characteristic of, an unsuccessful or less promising tissue regeneration, unsuccessful or less promising implantation and/or unsuccessful or less promising transplantation and/or the absence of cellular potency.

The indicative, or specific or characteristic, transcriptome and/or gene expression profiles mentioned in the two preceding examples enable, with particular advantage, a (more) reliable prognosis of a possible tissue regeneration success, implantation success or implant success and/or transplantation success or—in other words—of a possible tissue regeneration failure, implantation failure or implant failure and/or transplantation failure.

The transcriptome profile and/or gene expression profile which are/is indicative of, or specific for, or characteristic of, a successful tissue regeneration, successful implantation and/or successful transplantation and/or the presence of cellular potency are/is preferably determined by evaluating transcriptome profiles and/or gene expression profiles, originating from the transcriptome profiles, of the same cell type from patients for whom the tissue regeneration, implantation and/or transplantation has proceeded successfully, and/or for whom the cell type was potent.

The transcriptome profile and/or gene expression profile which are/is indicative of, or specific for, or characteristic of an unsuccessful or less promising tissue regeneration, unsuccessful or less promising implantation and/or unsuccessful or less promising transplantation and/or the absence of cellular potency are/is preferably determined by evaluating transcriptome profiles and/or gene expression profiles, originating from the transcriptome profiles, of the same cell type from patients for whom the tissue regeneration, implantation and/or transplantation has proceeded unsuccessfully or failed, and/or for whom the cell type was not potent.

The indicative transcriptome profile and/or gene expression profile mentioned in the preceding embodiments are/is preferably determined as part of a retrospective clinical follow-up or analysis of therapy results.

Furthermore, it is preferred when the indicative transcriptome profile and/or gene expression profile are/is determined by means of a search algorithm, preferably a computer-based search algorithm. This can be done using any (commercially) available evaluation software for transcriptome data, as presented in the application example, for example.

In a useful embodiment, RNA is isolated from the cells in order to carry out the transcriptome analysis. To this end, the cells are generally lysed in a chemical environment in which RNases (ribonucleases) are quickly denatured. Subsequently, the RNA is separated from the other cellular constituents such as, for example, DNA, proteins, sugars, lipids or the like. The isolation of the RNA can be based on an extraction or purification. For example, RNA can be isolated by means of the so-called guanidinium thiocyanate method with subsequent phenol/chloroform extraction.

The isolated RNA can be subjected to a quality analysis and/or quantity analysis. A qualitative determination of the isolated RNA can, for example, be achieved using a photometer, which usually requires only a very low sample amount in order to create a nucleic acid spectrum generally between 220 nm and 450 nm. Typically, what is measured is, firstly, the 260 nm/280 nm absorbance ratio and, secondly, the 260 nm/230 nm absorbance ratio. The 260 nm/280 nm absorbance ratio should be between 1.8 and 2.0. It allows, in particular, conclusions to be drawn about protein contamination. The 260 nm/230 nm absorbance ratio should be above 1.8 and indicates, in particular, contamination with solvents, salts and proteins. A further suitable method for quality analysis and/or quantity analysis is electrophoretic analysis, in which isolated RNA is separated by capillary electrophoresis in a special chip to obtain a so-called RNA electropherogram.

In a further example, noncoding RNA, more particularly noncoding and nonregulatory RNA, is removed as part of the transcriptome analysis.

Preferably, ribosomal RNA (rRNA) and/or transfer RNA (tRNA) are/is removed as part of the transcriptome analysis. This achieves, with particular advantage, an enrichment of coding RNA and/or regulatory RNA and allows the transcriptome analysis to be carried out without disruptive interference from other RNA. In other words, preference is given to performing the transcriptome analysis solely on the basis of coding RNA and/or regulatory RNA. Particularly preferably, a depletion of rRNA is performed.

For the removal of ribosomal RNA (rRNA), preparation kits from various manufacturers are fundamentally available. For example, rRNA can be removed by using the RIBOMINUS™ Eukaryote Kit (from Life Technologies), which is based on the selective removal of frequently occurring large ribosomal RNA molecules from the pool of total RNA. This is achieved by a hybridization of these rRNAs to sequence-specific biotin-labeled oligonucleotide probes. The hybridized complex is then immobilized and removed by streptavidin-coated magnetic beads. The rRNA-depleted product is generally subsequently additionally concentrated.

After removal of noncoding and, in particular, nonregulatory RNA, preferably ribosomal RNA (rRNA) and/or transfer RNA (tRNA), a quality analysis and/or quantity analysis can be carried out (again). In this respect, reference is made in full to the quality and/or quantity analyses described above in connection with the isolated RNA.

Particularly preferably, the transcriptome analysis is carried out solely on the basis of mRNA (messenger RNA). mRNA is processed RNA which, inter alia, has already passed through so-called splicing, i.e., no longer contains introns (noncoding segments) in contrast to pre-mRNA or natural DNA.

In a further example, the transcriptome analysis comprises a fragmentation of RNA, preferably mRNA. The fragmentation can be achieved by means of an enzymatic digest, generally by means of an RNase (ribonuclease) such as RNase III for example, and/or by physical means, for example by means of ultrasound. Fragments suitable for the method according to the invention can comprise 30 to 1000 nucleotides. Preferably, the fragmentation is carried out after removal of rRNA.

In a further example, the transcriptome analysis comprises carrying out a reverse transcription, i.e., the transcription of RNA, more particularly mRNA, into cDNA (complementary DNA). The transcription is preferably performed after a fragmentation of the RNA. Generally, the transcription is achieved using the enzyme reverse transcriptase. The product primarily obtained in the reverse transcription is a cDNA strand which is hybridized to the original RNA strand. The latter can then be degraded using RNase H. In a further step, a DNA-dependent DNA polymerase (via a primer) is used to synthesize a DNA strand complementary to the already existing single cDNA strand, with double-stranded cDNA being obtained.

In a further example, the transcriptome analysis comprises the replication or amplification of double-stranded cDNA. Preferably, the cDNA is replicated or amplified by means of the polymerase chain reaction (PCR), more particularly emulsion polymerase chain reaction (emulsion PCR).

A reverse transcription and a subsequent amplification of the cDNA obtained as part of the reverse transcription make it possible, with particular advantage, to create cDNA libraries.

In useful examples, a size selection of the double-stranded cDNA by polyacrylamide gel electrophoresis (PAGE) can be carried out prior to the replication or amplification.

In a further example, the cDNA is subjected to a sequencing method.

Preferably, the transcriptome analysis comprises a hybridization-based microarray or macroarray method, also referred to as DNA hybridization array method, or a sequence-based method, preferably a second-generation sequencing method.

Both the microarray or macroarray method and the sequence-based method allow, in each case, the expansion of gene expression analysis to a genomewide approach, by allowing the simultaneous detection of the differences in expression of several thousand genes in one experiment.

In terms of its functional principle, the microarray or macroarray method resembles conventional hybridization techniques in molecular biology such as, for example, Northern or Southern blot analyses. These methods utilize the property of nucleic acids to hybridize to one another in a sequence-specific manner. Hybridization is understood to mean the noncovalent bonding of two nucleic acid single strands complementary to one another, said bonding being primarily based on the formation of hydrogen bonds between the heterocyclic bases of the nucleic acid molecules.

In the microarray or macroarray method or the DNA hybridization array method, nucleic acids of known sequence, so-called probes, are applied to and immobilized on a support in a spatially resolved manner in a large number and at a high density, generally with the aid of a robot. These DNA hybridization arrays are subsequently hybridized to labeled nucleic acids. For the labeling, it is, for example, possible to incorporate radioactively or fluorescently labeled nucleotides during the reverse transcription of RNA, generally mRNA, into cDNA. Since a hybridization only takes place between complementary nucleic acid molecules, the intensity of the measured signal is proportional to the frequency of the hybridizations achieved. Since each position of a probe corresponds to a particular gene or gene segment, the signal intensity measured at said position provides a measure of the relative expression level of said gene. Depending on the number of available gene probes and the density at which they are applied to the support, it is possible using such arrays to simultaneously analyze several thousand genes.

The second-generation sequencing methods are no longer based on a separation of DNA via capillary electrophoresis, as in the case of the so-called Sanger method, but instead on a coupling of cDNA fragments to solid supports and the complementary binding of individual nucleotides or oligonucleotides, the binding thereof being confirmed using a high-resolution camera.

Preferably, in our methods, the transcriptome analysis comprises a second-generation sequencing method selected from the group comprising pyrosequencing, sequencing by synthesis, and sequencing by ligation.

In pyrosequencing, DNA fragments are hybridized via linker molecules, generally in the form of oligo-peptide adapters, onto beads (one fragment per bead). The DNA fragments are then replicated by means of a polymerase chain reaction (PCR). To this end, the beads enter an emulsion containing PCR reagents. The newly formed DNA copies as a consequence of the polymerase chain reaction are likewise caught on the beads. For the sequencing, the beads are subsequently distributed on appropriate titer plates, preferably PicoTiter plates, having wells containing enzymes and primers required for carrying out the sequencing. One after another, the four nucleotides deoxyadenosine triphosphate (dATP), deoxyguanosine triphosphate (dDTP), deoxycytidine triphosphate (dCTP) and deoxythymidine triphosphate (dTTP) are then added. With each incorporation of nucleotide, pyrophosphate is released, which, as ATP, stimulates for example the enzyme luciferase to convert luciferin into oxyluciferin and light. The corresponding wells of the titer plates light up. Since only one nucleotide is added per sequencing step, the sequence of the DNA fragments can thus be determined on the basis of the signal.

In the sequencing method "sequencing by synthesis", reversible terminator nucleotides are used. The DNA fragments to be sequenced are bound to the glass surface of a flow cell and replicated by means of a polymerase chain reaction (PCR). The PCR copies are fixed around the original DNA fragment, resulting in a group of identical molecules. The sequencing involves—similar to the Sanger method—reversible terminator nucleotides. The synthesis reagents (primer, DNA polymerase and four different fluorescent dye-labeled reversible terminator nucleotides) are added to the flow cell. If one of the four terminator nucleotides attaches to a DNA fragment, the fluorophore blocks further synthesis. The reaction stops briefly, dye and terminator nucleotide are cleaved, and the light signal is documented before a new round begins.

In the sequencing method "sequencing by ligation", the actual sequencing reaction takes place after an emulsion polymerase chain reaction (emulsion PCR) on beads. In a first round (of five in total), both universal sequencing primers (length n) and a mixture of four different octamer oligonucleotides are added to the reaction. Positions 1 and 2 of said octamers have defined bases (four of 16 possible dinucleotide pairs; in the five rounds, all 16 possible dinucleotides are used) which are coded by one of four fluorescent dyes. The appropriate octamer oligonucleotide hybridizes onto the PCR fragment and is ligated to the likewise hybridized sequencing primer. The fluorescence signal is measured and the dye together with the last three nucleotides removed. These steps are repeated several times, depending on DNA length (in the case of 30-35 bases, this would be 6-7 rounds, and, in the next cycle, bases 6/7, then 11/12, are interrogated). Lastly, all ligated oligo-primer constructs are removed (reset). A new round starts with a new sequencing primer of length n−1 and four other fluorescently labeled dinucleotides. Now, in the first cycle round, bases n−1 and 1 are thus identified, then bases 5/6, 10/11, etc. After three further rounds (primers n−2, n−3 and n−4), the sequence is available; each base has been checked by two different oligonucleotides.

With regard to an overview of the currently established high-throughput sequencing methods, reference is made to the publications by Niedringhaus et al. (Landscape of Next-Generation Sequencing Technologies, Anal. Chem. 2011, 83, 4327-4341) and Hurd et al. (Advantages of next-generation sequencing versus the microarray in epigenetic research, BRIEFINGS IN FUNCTIONAL GENOMICS AND PROTEOMICS. VOL 8. NO. 3. 174-183) and also to the article by Hollricher (Hochleistungs-Sequenzieren [High-performance sequencing], Laborjournal 2009, 4, 44-48), the disclosure content of which with respect to the sequencing methods described therein is in each case incorporated in the present description by express reference.

In a further example, the transcriptome analysis comprises an assembly or a joining together of the sequenced cDNA or cDNA fragments. This allows conclusions to be drawn about functional or evolutionary relationships and thus about the original sequence. The assembly can be carried out by appropriate bioinformatic methods familiar to those skilled in the art.

In a further example, the assembled cDNA fragments are subjected to a gene annotation, which allows an identification of information-bearing sequences, especially of differentially regulated genes. It is useful for the gene annotation to be supported by bioinformatic methods, by means of which patterns or profiles and relationships can be discovered and related to known knowledge, especially concerning metabolic and regulatory networks. Fundamentally, the analysis of these data requires a normalization before the actual processing, for example by clustering methods. If the data are in the form of quotients composed of measured values via a treatment experiment and a reference experiment, a normalization is generally achieved by logarithm formation. Other normalizations are, for example, based on vector norm, hierarchy, uniform variance or the so-called z-score. The last one is a method of deciding whether a particular value is significantly below, on or above a mean value. In this connection, a negative value is an indicator for values smaller than a mean value and a positive value is an indicator for values greater than a mean value. The analysis of the standard deviation then delivers additionally the significance of this deviation. Available for a visualization of these data are various software systems, which generally allow, firstly, a structuring of the data on the basis of different functional categories and, secondly, a visualization according to the categorization done. The assignment of function, or categorization, can be fundamentally achieved on the basis of available annotations in conjunction with known search algorithms or else by a combination of available annotations and individually found search algorithms. The basis of such search algorithms is usually formed by difference analyses, in which the gene expression pattern of a sample to be investigated is compared with reference samples depicting a particular pathophysiological phenotype. On the basis of these data, it is then possible to program search algorithms specifically tailored to the cell states to be identified.

Furthermore, this disclosure relates to the use of the transcriptome analysis, more particularly of transcriptome profiles and/or of gene expression profiles originating from a transcriptome or based on a transcriptome, for prognostically assessing tissue regeneration capacity and/or cellular potency and/or the prospects of success of an implantation, more particularly cell implantation, and/or transplantation. To avoid unnecessary repetition, reference is made in full to the description so far with regard to further features and advantages.

Further features and advantages of our methods are revealed by the below-described examples with reference to figures and descriptions. Individual features of our methods can be realized alone or in combination with one another. The described examples merely serve to elucidate our methods and provide a better understanding and are not to be understood to be limiting in any way.

EXAMPLES

1. Material and Methods
1.1 Structure of the Study

What was carried out was a retrospective survey of initial results, adverse effects and changes in the starting state with regard to pain, functioning and swellings in a patient population as defined below. Further analyses were performed in order to investigate the influences of patients, production and cell biology properties on safety and patient results. The clinical and surgical procedures, including indications and rehabilitation, were defined in standard operating procedures (SOPS). Surgeons were trained in the surgical techniques for cartilage recovery and implantation surgery before they used the implant for the first time. After the patients had given their informed consent, the treatment indication was confirmed by arthroscopy. In the affected joint, two to three cartilage-bone pieces were removed from the fossa intercondylaris (a non-stressed region) using a sterile and validated standard trephine (Aesculap A G, Tuttlingen, Germany, cutting diameter: 4 mm).

1.2 Clinical Data Collection

The surgeon of each patient was asked to complete a data collection sheet which comprised medical history (etiology), basic demographic data (age, gender) and period between surgical procedure and last contact with patient. Together with the patient, pain intensity, functioning and swellings were assessed on a 10-point scale both in the consultation before the procedure and after the procedure. The result assessment scale was adapted from the visual analog scale (VAS). Higher values indicate better results (i.e., 10 means "no pain", "no swelling", "no functional impairment"). This 10-point result grading was carried out by each surgeon in a patient consultation and was used as an early indicator for further clinical progression. The participating surgeons were also asked to specify all adverse effects which occurred and, similarly, any treatment which was subsequently required. The questionnaire did not investigate whether the patients responded inadequately to an earlier arthroscopic or other surgical cartilage repair method. In extreme cases, the undesired effect was an implant failure as a result of nonhealing or tear-out.

1.3 Study Population

The survey was carried out at 61 centers in Germany, in which 433 patients were treated. Data were reported back for a total of 422 patients (97.4%). The remaining 11 patients were excluded from the rest of the study and the RNA analyses. Among the 422 patients, there were 140 women and 282 men. Their average age was 33.4 years (minimum: 14.7 years, maximum: 66.3 years). The majority of the primary cartilage defects (damage from grade III to IV according to the classification of the International Cartilage Repair Society (ICRS)) were established on the medial femoral condyle of the knee (68.5%), followed by the lateral condyle (14.9%), the retropatellar region (10.2%), the trochlea (5%) and the tibia (0.2%). In six patients (1.4%), the defect was established on the talus. The majority of the patients had a single defect (93%). The defect size varied between 1 and 20 cm$^2$. The average size was 5.9 cm$^2$. The average duration of patient aftercare was 6.9 months. Of a total of 83 patients, at least one year elapsed since the surgical procedure up to the day of the last visit registered by the surgeon (Table 1).

TABLE 1

Study population (422 patients)

| | | Absolute number | Percent |
|---|---|---|---|
| Gender | Male | 282 | 66.8% |
| | Female | 140 | 33.2% |
| Age | Mean | 33.4 | |
| | SD | 10.0 | |
| | Range | 14.7-66.3 | |
| Duration of patient after-care in days | Mean | 210 | |
| | SD | 185 | |
| | Range | 0-921 | |
| Diagnosis | Chronic damage | 24 | 5.7% |
| | Degenerative defect | 144 | 34.1% |
| | Osteochondritis dissecans | 123 | 29.1% |
| | Traumatic defect | 137 | 32.5% |
| Location of primary defect | Lateral femoral condyle | 63 | 14.9% |
| | Medial femoral condyle | 289 | 68.5% |
| | Patella | 43 | 10.2% |
| | Talus | 6 | 1.4% |
| | Tibia | 1 | 0.2% |
| | Trochlea | 21 | 5.0% |
| Primary defect size (cm$^2$) | Mean | 5.9 | |
| | SD | 3.1 | |
| | Range | 1-20 | |
| Number of defects treated | 1 | 391 | 92.7% |
| | 2 | 29 | 6.9% |
| | No data | 2 | 0.5% |

Table 1 shows the study population with the corresponding patient features. The features are assigned absolute patient numbers and, where applicable, percentage shares. A multiple diagnosis was possible for one patient, with the defects affecting more than one region.

1.4 Culturing

After removal from bone, mineralized cartilage and superficial cartilage, chondrocytes were isolated from the remaining cartilage by mechanical and enzymatic extraction, conditioned according to standard methods, and multiplied in vitro as a primary culture in equipment permitted according to good manufacturing practice (GMP) (TETEC AG, Reutlingen, Germany). The steps comprised, after cell isolation, a multiplication of cells in culture medium enriched with autologous serum, harvesting by trypsinization and colonization in the scaffold (NOVOCART® Basic), and this took place 21 days after the arthroscopy for cartilage recovery. The scaffold was colonized with a mean cell dose of $1.36 \times 10^6$ cells per $cm^2$. Typically, cells were directly applied from the primary culture. Under special circumstances (e.g., patient disease), cells were cryopreserved before use and administered from secondary cultures (less than 10% of cases).

1.5 High-Throughput RNA Sequencing

20 RNA samples from the batches described in the preceding section were analyzed, and of these, ten came from clinically successful treatments and ten were obtained from patients with negative results. Each sample was assigned a unique barcode sequence and aliquots of the barcoded samples were, depending on the patient result (positive results, negative results), combined into two groups.

From each sample, 1 to 10 µg of the total RNA of chondrocytes was used as starting material. The total RNA was analyzed with regard to quantity and integrity using an Agilent RNA 6000 Nano Chip (5067-1511) on instrument model Bioanalyzer 2100. A depletion of ribosomal RNA (rRNA) was carried out using 2-3 runs with the RIBOMINUS™ Eukaryote Kit for RNA-Seq (A10837-08, life technologies) according to the protocol from the manufacturer. A concentration was carried out using the RIBOMINUS™ Concentration Module (K1550-05, life technologies). The efficiency of rRNA removal was checked and determined in an aliquot run on an Agilent RNA 6000 Nano Chip (5067-1511) on instrument model Bioanalyzer 2100, with a complete elimination of rRNA peaks being seen.

A library was created using the SOLiD™ Total RNA-Seq Kit (4445373, life technologies) according to the protocol from the manufacturer. In brief, 10 to 100 ng of RNA after ribosome depletion were firstly fragmented by a 10-minute long digest at 37° C. with RNase III and purified again using the RIBOMINUS™ Concentration Module (K1550-05, life technologies) and eluted in 12 µl of RNase-free water. The fragment size was checked for the optimal size range for the SOLiD4 instrument (150 to 200 nucleotides), and again an aliquot run was performed on an Agilent RNA 6000 Nano Chip (5067-1511) on instrument model Bioanalyzer 2100.

For the construction of cDNA libraries, the RNA fragments were linked to adapters in a strand-specific manner and converted into double-stranded cDNA libraries, with use being made of a reverse transcription followed by a size selection using PAGE and amplification by PCR. During the PCR amplification, barcode sequences were inserted, with the 3'-adapter primer bearing a specific barcode-specific overhang. This method avoids barcode distortions which have been reported when barcode adapters are directly linked to the library. Once again, the fragment size was checked for the region of 150 to 200 nucleotides in an aliquot run on an Agilent DNA 1000 Chip (5067-1504) on instrument model Bioanalyzer 2100.

The concentration measurements of the Bioanalyzer were used for the calculation and equimolar mixing of barcoded samples S1-S10 (good clinical results) and S11-S20 (negative clinical results) (in each case barcodes 1-10). An emulsion PCR (emPCR) was carried out for each combined library, in each case on an E20 scale according to the recommendations from the manufacturer with a final library concentration of 0.5 µM. The breaking of the emulsion and the washing of beads and also the enrichment of beads were performed manually according to the protocol from the manufacturer. The quality and quantity of the template beads were measured in a workflow analysis (WFA) run of 15 million enriched template beads on a SOLiD4.0 instrument. In both libraries, the signal-to-nose ratio was 4% and the P2/P1 ratio was 100%, indicating a high percentage of monoclonal beads. 158 million template beads of the libraries were applied in each case to a quad field (¼) of a SOLiD4.0 carrier and sequenced by ligation from adapter P1, and so a 50 bp fragment reading record was obtained.

1.6 Data Creation

Data relating to adverse effects and patient results were collected and entered into a spreadsheet. Quality control data of production and also covariables (features relating to demography, patient and product release) were entered into the same database. All the entered data were checked for agreement.

1.7 Statistics and Covariant Analysis of Individual Parameter Data

Summary statistics with mean values, standard deviations, ranges and confidence intervals were used in order to show the amounts of adverse effects, efficacy results and patient characteristics. The release characteristics of each product were compared with the survey data in order to identify associations between implant production features and patient results. A number of chi-squared tests and regression models was created in order to check for associations between production characteristics or release characteristics and the five result measurements in the patient safety survey comprised: implant-related adverse effects (defined as pooling of implant failure, detachment, hypertrophy, arthrofibrosis, adhesions, chondromalacia, articular infections and appearance of free articular bodies), further operations (any reason) and changes in the starting state with regard to pain, functioning and swellings. Regressions relating to the modeling of the association between biomarkers and an interesting result were simultaneously fitted both for each biomarker and all biomarkers. A logistic regression modeling was used in order to determine the influence of the independent covariants on the appearance of implant-related adverse effects and the appearance of further operations. Linear models were used to model the changes in the starting state with regard to pain, functioning and swellings. At 0.05, p-values were assumed as significant. All the regression models comprised the period from the surgical procedure up to the last medical appointment with the patient, since this was suspected of being a significant independent predictive value for the results.

1.8 Statistical Analysis of all Transcriptome Data

Using the Whole Transcriptome Analysis Pipeline of the BIOSCOPE™ 1.32 software (Applied Biosystems), reading sequences were mapped onto the human genome (UCSC version HG 19). Proceeding from the annotations of the UCSC refSeq (downloaded on 7 Nov. 2010), RPKM values of expression for genes were calculated. In brief, RPKM values (reads per kilobase exon model per million mapped) are the number of sequenced segments mapping onto the exons of a given transcription, normalized by the sequencing depth per sample (total segment number) and the length (bp) of all exons. These values were used for the initial determination. The scale normalization method described by Bullard et al. (J. H. Bullard, E. Purdom, K. D. Hansen, S. Dudoit, Evaluation of statistical methods for normalization and differential expression in mRNA-Seq experiments.

BMC Bioinformatics 11: 94 (2010)) was used to eliminate sample-specific technical distortions and the expression values obtained were mapped onto a logarithmic scale. Samples were clustered using the neighbor joining algorithm (N. Saitou and M. Nei, The neighbor-joining method: a new method for reconstructing phylogenetic trees. Mol. Biol. Evol. 4 (4): 406-425 (1987)), which is based on the Pearson correlation distance between their entire transcriptome expression profiles. The nonparametric rank product method (R. Breitling, P. Armengaud, A. Amtmann, P. Herzyk, Rank products: a simple, yet powerful, new method to detect differentially regulated genes. FEBS Letters 573 (1): 83-92 (2004)) was used in order to check for differential expression, yielding pfp values (percent false positive values, a measure comparable with FDR-corrected p-values), and transcripts with pfp<0.05 and an absolute value of fold change greater than 0.9 (i.e., doubled or halved expression) were considered to be significant differential expression. The differentially expressed protein-encoding transcripts were used in order to check for an enrichment of specific functional categories (overrepresentation analysis, hypergeometric test, p-values corrected for false discovery rate). For all the analyses, use was made of the technique described by Mayday (F. Battke, S. Symons, K. Nieselt, Mayday—Integrative analytics for expression data. BMC Bioinformatics 11 (1): 121 (2010)). Using the Integrative Genomics Viewer IGV (J. T. Robinson, H. Thorvaldsdottir, W. Winckler, M. Guttman, E. S. Lander, G. Getz, J. P. Mesirov, Integrative genomics viewer. Nat. Biotech. 29: 24-26 (2011)), the segments of individual genes of interest were studied in detail.

2. Results 2.1 Changes in the Starting State for the Patient Results

Prior to a surgical procedure and in following patient visits, the physicians determined articular pain, functioning and swellings on a 10-point scale, with higher values indicating better results. Patients who gave answers both in relation to questions before the procedure and after the procedure achieved significant improvements with respect to the starting state ($p<0.0001$, Wilcoxon signed-rank test) in all three measurements. The mean duration since the surgical procedure was 6.9 months (range: 2 to 30 months), and this is a noticeably shorter time scale than specified in the majority of other summaries of ACI results. The retrospective study contributed important aspects to the present knowledge relating to the repair of articular cartilage. In the subgroup of 83 patients with at least 12 months since their surgical procedure, it was reported that they exhibited stronger changes on average in all three result measurements than the entire patient population (Table 2).

TABLE 2

Individual result measurement

| Result measurement | | All patients (N = 422) | | | | | Investigation period > 1 year (N = 83) | | | | |
|---|---|---|---|---|---|---|---|---|---|---|---|
| | | Min | Mean | Max | SD | N | Min | Mean | Min | SD | N |
| Pain | Pre-operative | 1 | 3.4 | 10 | 1.3 | 412 | 2 | 3.4 | 9 | 1.2 | 82 |
| | Post-operative | 1 | 7.0 | 10 | 2.0 | 382 | 2 | 7.2 | 10 | 1.9 | 80 |
| | Change | −5 | 3.8 | 8 | 2.1 | 376 | 2 | 3.9 | 8 | 2.1 | 80 |
| Swelling | Pre-operative | 1 | 5.3 | 10 | 2.4 | 411 | 1 | 5.1 | 10 | 2.4 | 82 |
| | Post-operative | 1 | 7.7 | 10 | 1.9 | 382 | 4 | 8.1 | 10 | 1.6 | 80 |
| | Change | −7 | 2.5 | 9 | 2.6 | 375 | −3 | 3.1 | 8 | 2.2 | 80 |
| Functioning | Pre-operative | 1 | 4.2 | 10 | 1.8 | 412 | 2 | 4.4 | 10 | 2.0 | 82 |
| | Post-operative | 2 | 7.3 | 10 | 1.8 | 380 | 2 | 7.8 | 10 | 1.6 | 80 |
| | Change | −7 | 3.2 | 8 | 2.3 | 374 | −7 | 3.6 | 8 | 2.4 | 80 |

2.2 Appearance of Adverse Effects

Table 3 shows the appearance of reported adverse effects. The appearance of implant failure was 3.1% in the entire patient population and 6% in the subgroup of patients for whom at least 12 months had elapsed since their procedure. In general, the reported numbers of cases of implant-related complications were low for the entire patient population. Detachment (delamination), arthrofibrosis and hypertrophy were observed in 1.7%, 2.4% and 0.7%, respectively. Altogether 36 patients (8.5%) required a further operation and/or correction. The most common adverse effects reported in patients who required further operations were implant failure (13, the ten samples further investigated by transcriptome analysis originated from these cases), detachment (6), arthrofibrosis (7), synovitis (7), adhesions (5) and pain (6). The subgroup of 83 patients for whom at least 12 months had elapsed since their procedure exhibited a further operation rate of 13.3%. The majority of the further operations were carried out arthroscopically.

TABLE 3

Reported complications

| Complication | All patients (N = 422) | | | Investigation period > 1 year (N = 83) | | |
|---|---|---|---|---|---|---|
| | Cases | % | 95% CI** | Cases | % | 95% CI** |
| Implant-related complications*** | | | | | | |
| Implant failure | 13 | 3.1% | 1.7% 5.2% | 5 | 6.0% | 2.0% 13.5% |
| Delamination | 7 | 1.7% | 0.7% 3.4% | 2 | 2.4% | 0.3% 8.4% |
| Hypertrophy | 3 | 0.7% | 0.2% 2.1% | 1 | 1.2% | 0.0% 6.5% |
| Arthrofibrosis | 10 | 2.4% | 1.1% 4.3% | 2 | 2.4% | 0.3% 8.4% |
| Adhesions | 7 | 1.7% | 0.7% 3.4% | 2 | 2.4% | 0.3% 8.4% |
| Free articular bodies | 1 | 0.2% | 0.0% 1.3% | 1 | 1.2% | 0.0% 6.5% |
| Deep (artic-ular) infection | 3 | 0.7% | 0.2% 2.1% | 0 | — | |
| Chondromalacia | 2 | 0.5% | 0% 1.7% | 0 | — | |
| Further complications | | | | | | |
| Effusion | 32 | 7.6% | 5.2% 10.5% | 6 | 7.2% | 2.7% 15.1% |
| Pain | 29 | 6.9% | 4.7% 9.7% | 7 | 8.4% | 3.5% 16.6% |
| Synovitis | 14 | 3.3% | 1.8% 5.5% | 3 | 3.6% | 0.8% 10.2% |
| Hematoma/ hemarthrosis | 7 | 1.7% | 0.7% 3.4% | 5 | 6.0% | 2.0% 13.5% |
| Stiffening | 1 | 0.2% | 0.0% 1.3% | 1 | 1.2% | 0.0% 6.5% |
| Superficial infection | 2 | 0.5% | 0.0% 1.7% | 0 | — | |

2.3 Association Between Results and Independent Risk Factors

The size of all treated defects did not show any correlation with any of the measured patient results. For the change in the starting state in the case of the functioning of the patient, a significant association with patient age was found (i.e., in the case of a lower age, greater improvements on average were apparent, p=0.004, not shown). Table 4 specifies the results of chi-squared tests relating to the association of the location of the primary defect to the appearance of implant-related adverse effects. It was found that both the appearance of implant-related adverse effects and of further operations is largely independent of the location of the primary defect, with the exception of patellar defects. In any case, for an affected individual, the probability of such an event was greater when the primary defect was situated on the patella (p<0.0001).

TABLE 4

Implant-related complications and further operations depending on the location of the defect

| Location | Defect in this position | | | Defect not in this position | | | p-value |
|---|---|---|---|---|---|---|---|
| | Cases | N | % | Cases | N | % | |
| Implant-related complications* depending on location of defect | | | | | | | |
| Medial femoral condyle | 22 | 289 | 7.6% | 14 | 133 | 10.5% | 0.32 |
| Lateral femoral condyle | 3 | 63 | 4.8% | 33 | 359 | 9.2% | 0.25 |
| Trochlea | 1 | 21 | 4.8% | 35 | 401 | 8.7% | 0.53 |
| Patella | 11 | 43 | 25.6% | 25 | 379 | 6.6% | <0.0001 |
| Tibia | 0 | 1 | 0.0% | 36 | 421 | 8.6% | 0.76 |
| Talus | 0 | 6 | 0.0% | 36 | 416 | 8.7% | 0.45 |
| Further operations depending on location of defect** | | | | | | | |

TABLE 4-continued

Implant-related complications and further operations depending on the location of the defect

| Location | Defect in this position | | | Defect not in this position | | | p-value |
|---|---|---|---|---|---|---|---|
| | Cases | N | % | Cases | N | % | |
| Medial femoral condyle | 20 | 289 | 6.9% | 16 | 133 | 12.0% | 0.08 |
| Lateral femoral condyle | 3 | 63 | 4.8% | 33 | 359 | 9.2% | 0.25 |
| Trochlea | 1 | 21 | 4.8% | 35 | 401 | 8.7% | 0.53 |
| Patella | 12 | 43 | 27.9% | 24 | 379 | 6.3% | <0.0001 |
| Tibia | 0 | 1 | 0.0% | 36 | 421 | 8.6% | 0.76 |
| Talus | 0 | 6 | 0.0% | 36 | 416 | 8.7% | 0.45 |

Table 5 specifies the results of chi-squared tests relating to the association between the classification of cartilage injuries and the appearance of implant-related adverse effects and further operations. In implant-related adverse effects, for an affected individual, the

TABLE 5

Implant-related complications and further operations depending on the nature of the defect

| Nature of defect | Defect of this type | | | Other defect | | | p-value |
|---|---|---|---|---|---|---|---|
| | Cases | N | % | Cases | N | % | |
| Implant-related complications* depending on nature of defect | | | | | | | |
| Chronic damage | 1 | 24 | 4.2% | 35 | 398 | 8.8% | 0.43 |
| Degenerative defect | 20 | 144 | 13.9% | 16 | 278 | 5.8% | 0.005 |
| Traumatic defect | 11 | 137 | 8.0% | 25 | 285 | 8.8% | 0.80 |
| Osteochondritis dissecans | 5 | 123 | 4.1% | 31 | 299 | 10.4% | 0.04 |
| Further operations depending on nature of defect | | | | | | | |
| Chronic damage | 1 | 24 | 4.2% | 35 | 398 | 8.8% | 0.43 |
| Degenerative defect | 17 | 144 | 11.8% | 19 | 278 | 6.8% | 0.08 |
| Traumatic defect | 13 | 137 | 9.5% | 23 | 285 | 8.1% | 0.63 |
| Osteochondritis dissecans | 5 | 123 | 4.1% | 31 | 299 | 10.4% | 0.04 |

Table 6 shows associations between patient results and cell culture variables, on the one hand, and mRNA expression values of six selected marker genes (cf. section 2.4.1), on the other hand, as multivariant p-values. Significant relationships and marginal trends are highlighted. A temporary cryopreservation of the cells before an implantation did not show any association with an intensified appearance of implant-related complications (IRC) or with any of the other result measurements (further operation FO, pain, functioning, swelling). With regard to cell viability, the same results were observed. However, a low number of administered cells was significantly associated with a further operation (FO) (p=0.06; Table 6).

TABLE 6

Relationship between patient results and cell culture variables or mRNA expression values of six selected marker genes

| Cell culture variables | IRC | FO | Pain | Functioning | Swelling |
|---|---|---|---|---|---|
| Cryopreservation | 0.98 | 0.98 | 0.59 | 0.78 | 0.13 |
| Cell viability upon harvesting | 0.56 | 0.13 | 0.55 | 0.38 | 0.76 |
| Cell count (log 10) | 0.30 | 0.06 | 0.47 | 0.37 | 0.36 |
| PCR expression measurement | | | | | |
| Aggrecan | 0.14 | 0.44 | 0.61 | 0.50 | 0.62 |
| BSP-2 | 0.11 | 0.14 | 0.76 | 0.78 | 0.90 |
| Collagen I | 0.49 | 0.70 | 0.53 | 0.79 | 0.27 |
| Collagen II | 0.08 | 0.08 | 0.42 | 0.90 | 0.29 |
| Interleukin-1β | 0.08 | 0.20 | 0.26 | 0.19 | 0.24 |
| FLT-1 | 0.02 | 0.03 | 0.21 | 0.67 | 0.81 |

2.4 Expression Data
2.4.1 Specific Gene Expression

Quantitative real-time PCR (qRT-PCR) was used to determine the expression of six selected marker genes: aggrecan (ACAN), an integral constituent of the extracellular cartilage matrix; type I collagen (COL1A2), which usually does not occur in cartilage tissue; cartilage-specific type II collagen (COL2A1); interleukin-1β (IL-1β), an inflammatory cytokine; FLT-1, an isoform of a vascular endothelial growth factor receptor; and bone sialoprotein BSP-2, a bone growth factor. The reason for selecting the last two mentioned genes was because complications can result especially from a vascularization of the implanted cartilage tissue or from a formation of osteophytes within the implanted cartilage tissue.

Figure 1A:
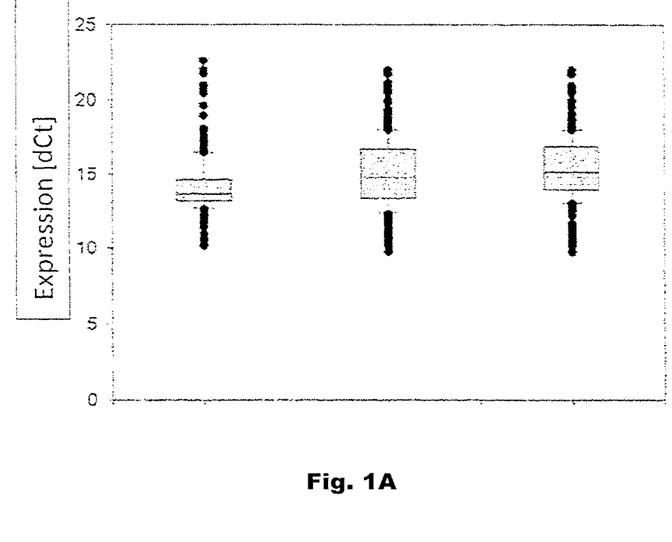
Figure 1B:
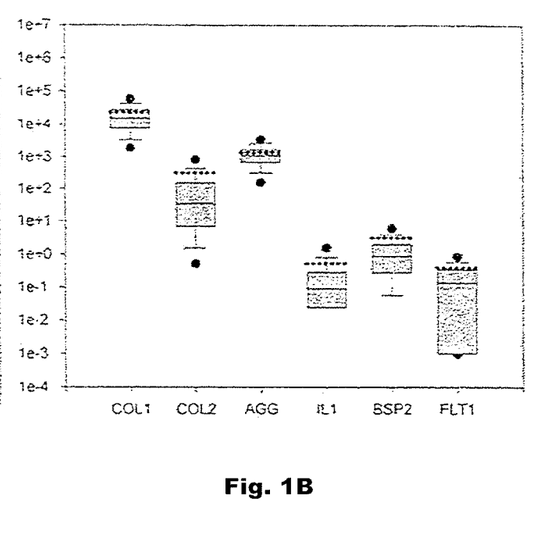

The expression values (dCt) of these six marker genes are depicted in FIG. 1B and show significant differences. The most stable mRNA levels, which vary within one order of magnitude among all 422 samples, were found for aggrecan. The greatest variations, within three orders of magnitude, with an altogether very low detection level, occurred for FLT-1. For type I collagen for example, it was possible to calculate on average 1000 mRNA transcripts per cell, whereas in the case of FLT-1, only 10 mRNA transcripts per 1000 cells were calculated. For comparison, there are, for example, at least 500 times more FLT-1 mRNA transcripts present in human venous endothelial cells cultured in vitro.

Despite these variations, it was nevertheless possible to observe significant or at least marginal correlations between some of these marker genes and the clinical result (Tables 6 and 7). For instance, it was possible to establish a significant association between implant-related complications (IRC) and elevated FLT-1 expression levels in multiplied chondrocytes (p=0.02, Table 6). In contrast, it was possible to determine only a marginal relationship for elevated IL-1β levels and lowered type II collagen levels (both p=0.08, Table 6). However, taking into account all the marker genes in the calculation models, it was possible to find for IL-1β (p=0.02, Table 6) and FLT-1 (p=0.08, Table 6) a significant or marginal relationship with respect to IRC.

According to Table 7, which shows for the six marker genes not only the regression coefficients but also the multivariant p-values taking into account the elapsed time since the procedure, it was not possible to classify the expression of any of the marker genes as significant with respect to pain, functioning and swelling. The coefficients for the patient results IRC and FO (further operation) were calculated by logistic regression; the coefficients for pain, functioning and swelling were calculated by means of linear regression. The p-values (second row) indicate the significance of the relationship in question, and significant relationships and marginal trends are highlighted.

TABLE 7

Multivariate analysis of the relationship between patient results and the time since the procedure or the mRNA expression values of six selected marker genes

| Variable | IRC | FO | Pain | Functioning | Swelling |
|---|---|---|---|---|---|
| Time since procedure | 1.057 | 1.064 | 0.0084 | 0.055 | 0.060 |
| | 0.037 | 0.017 | 0.644 | 0.0049 | 0.0059 |
| PCR expression measurement | | | | | |
| Aggrecan | 1.141 | 0.962 | 0.105 | −0.099 | 0.087 |
| p = | 0.492 | 0.836 | 0.343 | 0.397 | 0.506 |
| BSP-2 | 1.086 | 1.078 | −0.018 | −0.013 | −0.0085 |
| p = | 0.161 | 0.177 | 0.607 | 0.730 | 0.837 |
| Collagen I | 0.901 | 0.973 | 0.015 | 0.049 | 0.057 |
| p = | 0.426 | 0.835 | 0.849 | 0.564 | 0.556 |
| Collagen II | 1.095 | 1.112 | −0.034 | 0.015 | −0.054 |
| p = | 0.166 | 0.107 | 0.347 | 0.698 | 0.216 |
| Interleukin-1β | 1.151 | 1.112 | −0.044 | −0.049 | −0.054 |
| p = | 0.029 | 0.083 | 0.197 | 0.177 | 0.179 |
| FLT-1 | 1.106 | 1.102 | −0.033 | −0.0096 | −0.0041 |
| p = | 0.062 | 0.070 | 0.222 | 0.739 | 0.901 |

2.4.2 Genomewide Expression

Figure 2:
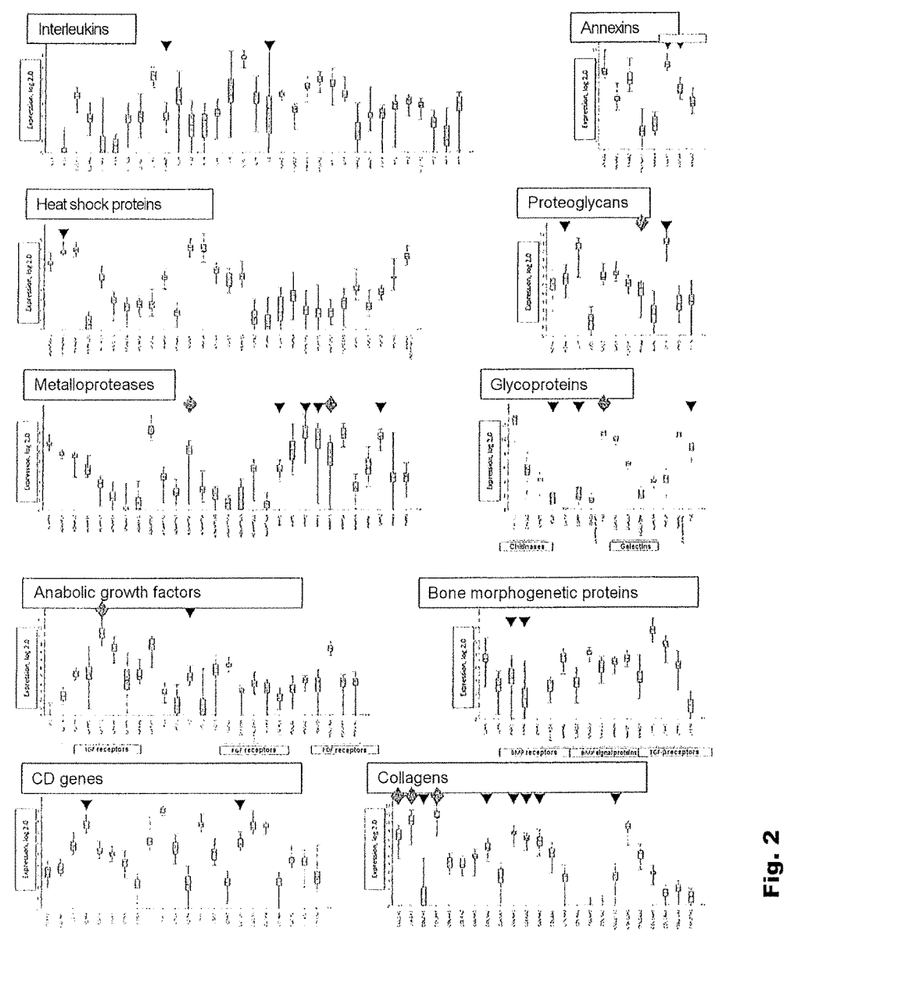

The entirety of the captured expression data comprised about 30,000 genes with a large variety of exon data and yielded more than 200 million individual data segments. For the group S1-10 (good clinical results), 42, 716, 671 segments (75.3%) were unambiguously mapped, 3, 828, 740 (6.7%) were spanning exon junctions, 3, 791, 685 of the exon junctions were known and 37,055 were new. For the group S11-20 (implant failure), altogether 43, 429, 958 segments (76.0%) were unambiguously mapped, 3,991,606 segments (7.0%) were spanning exon junctions, 3,958,041 of the exon junctions were known and 33,565 were new. The mapped segments were used for calculating RPKM values ("reads per kilobase per million mapped reads" values) with BIOSCOPE™ 1.3 for each exon present in the UCSC refSeq database (downloaded on Jul. 11, 2010). A first RPKM survey was performed using gene families, with family members "typical" for chondrocytes being considered, for example collagens (with type II, IX and XI collagens as "cartilage collagens") or proteoglycans (with aggrecan (ACAN) as typical representative) (FIG. 2). The data are shown graphically, with the standard deviations indicating the exon variability. In addition, the expression values spanned several orders of magnitude and could only be shown on a logarithmic scale, as in FIG. 2. The results immediately show that the classic "chondrocytic" phenotype does not dominate the results. A further analysis of other gene families including, for example, IGF-related or PDGF-NEGF-related genes, confirms this presumption. An expression of the interleukin cytokines was diversified. The expression of these growth factors became even more complex when complementary binding proteins or the associated receptors were used. Equally, the transcription of the expanded clusters of metalloprotemases is very broad (FIG. 2).

2.5 Calibration of Transcriptome Data by qRT-PCR

Figure 3:
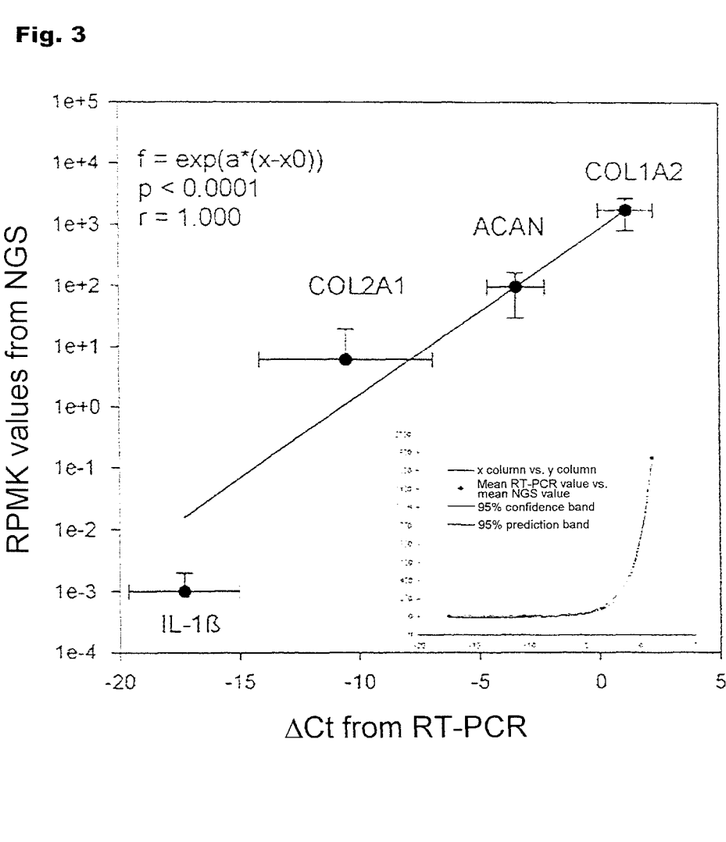
FIG. 3 shows the correlation analysis between qRT-PCR and RNA sequencing (NGS, next-generation sequencing) on the basis of the expression data of COL1A2, COL2A1, ACAN and IL-1$\beta$. The expression values for COL1A2, COL2A1, ACAN and IL-1$\beta$ were obtained, firstly, by means of conventional qRT-PCR from 422 samples (cf. Table 1) and, secondly, by means of NGS-based RNA sequencing from 20 samples. $\Delta$Ct values and RPKM expression values are shown logarithmically. The secondary figure shows the plot of the RPKM expression values before their logarithmic conversion, their very good correlation being even more clearly discernible.

To estimate the comparability of data in the two methods, a correlation analysis was performed on the basis of the expression data of COL1A2, COL2A1, ACAN and IL-1β (cf. FIG. 1B). These genes show typical expression values in chondrocytes within the range of seven powers of ten. The correlation of the values from the two methods was successful and yielded a correlation coefficient of 1.0 in an exponential function (FIG. 3).

2.6 Correlation Between Transcriptome Data and Clinical Results

Figure 4:
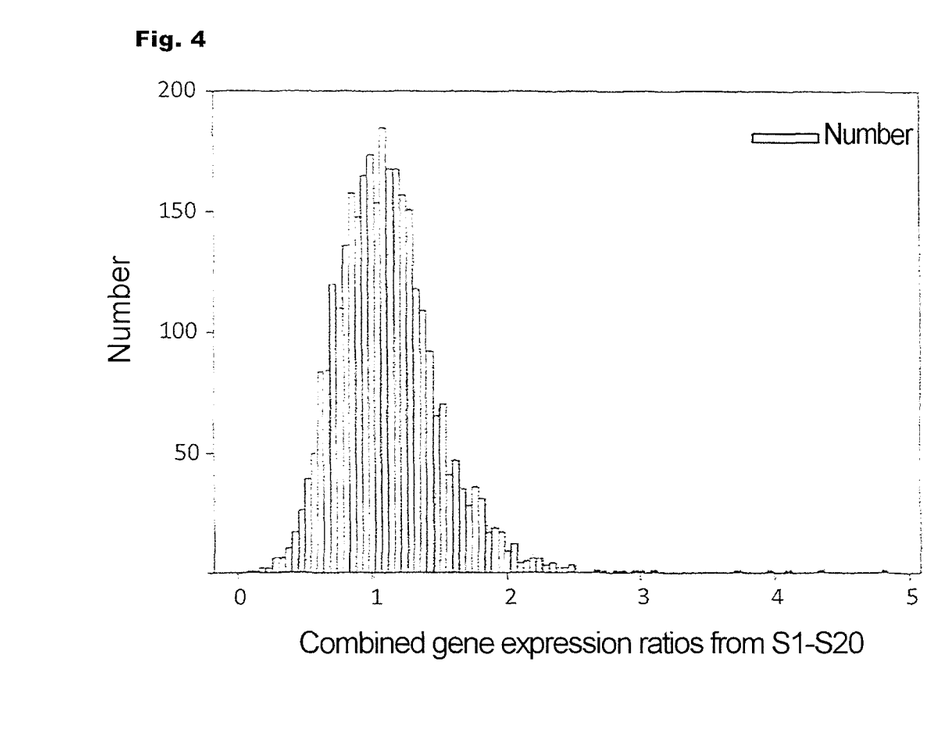
FIG. 4 shows the distribution of the numerical values for the gene expression ratios of the 3114 most highly expressed genes in the form of a histogram. The numerical values were obtained from the ratio of the averaged RPKM values of each transcribed gene from the group having good clinical results (S1 to S10) in relation to the mean value from the group having implant failure (S11 to S20). Numerical values >1 correlate with good clinical results. Numerical values <1 correlate with implant failure. Each bar represents 1/100 of the entire captured range (smallest numerical value: 0.006; largest numerical value: 4.9).

To obtain information about specific patterns which are (hypothetically) related to the clinical results, two evaluation methods were selected. In a first approach, the expression ratio for the averaged RPKM value of each transcribed gene from the group with good clinical results (S1 to S10) in relation to the mean value from the group with implant failure (S11 to S20) was determined. This yielded a list of numerical values >1, which have a positive correlation with good results, in relation to numerical values <1, which have a positive correlation with implant failure. Numerical values close to 1 indicate genes which behave neutrally in relation to the results. The results were shown as a histogram in FIG. 4. The histogram contains values for the 3114 most strongly expressed genes. 1803 values were >1, 1311 values were <1. Among these, 62 values were >2, meaning a twofold stronger expression in the group with good results S1-10, and 70 values were <0.5, meaning a twofold stronger expression in the group with implant failure. In other words, these two gene clusters are candidates for a restricted list of quality parameter genes for following studies. The list does not contain regulatory RNAs.

Figure 5:
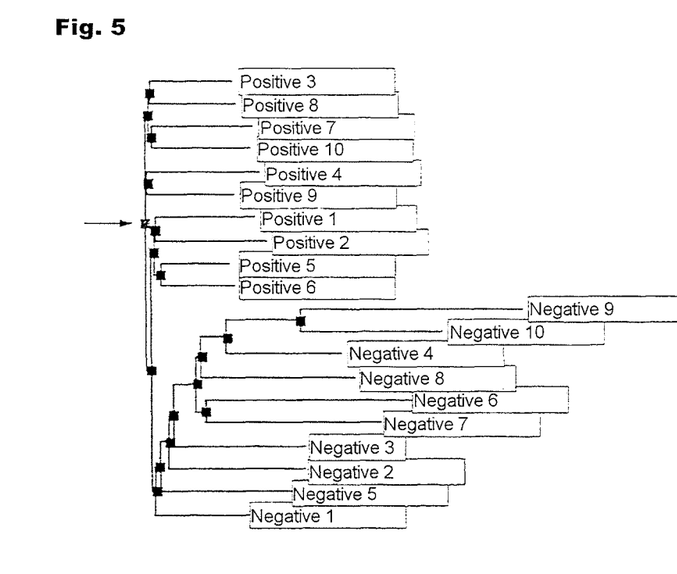
Figure 6A:
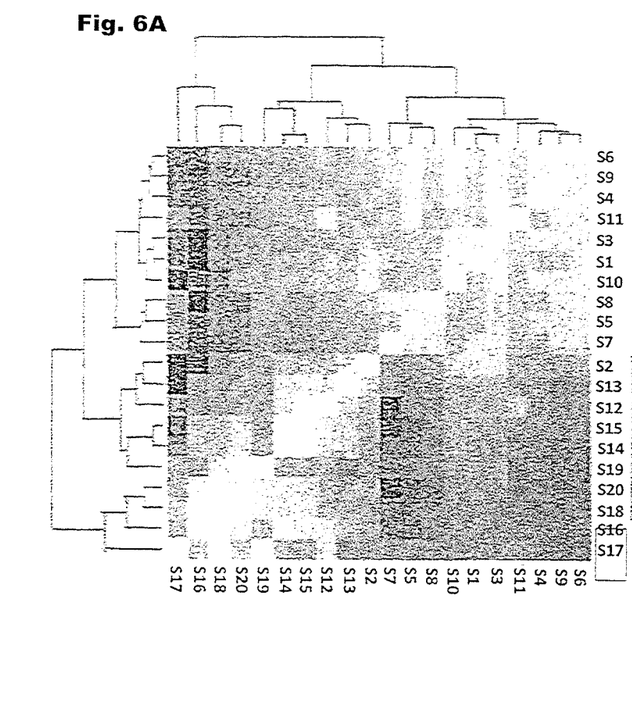
FIG. 6A shows a heatmap evaluation of the Pearson correlation cluster analysis from the RPMK numerical values of samples S1 to S20. The values were arranged according to their relationship, with closely related expression patterns being close together. What was considered here were the complete genes with all their exons.
Figure 6B:
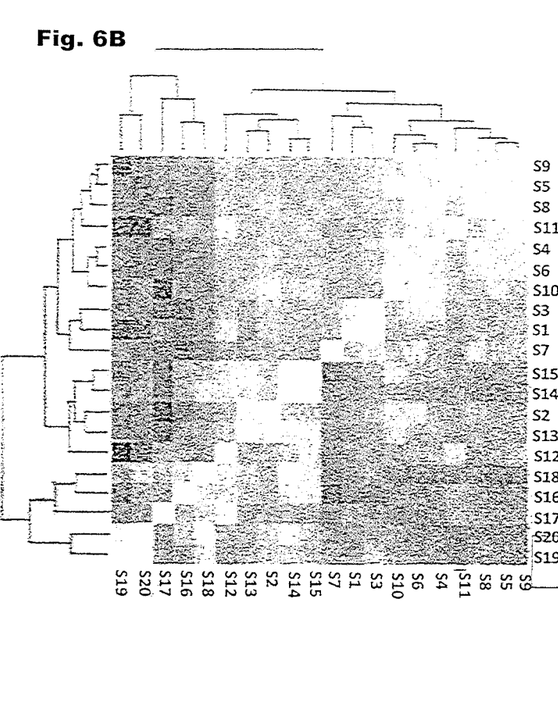
FIG. 6B shows a heatmap evaluation of the Pearson correlation cluster analysis from the RPMK numerical values of samples S1 to S20. The values were arranged according to their relationship, with closely related expression patterns being close together. The exons were analyzed individually and independently of the mRNA structure. Apart from S2 and S11, it was possible with this evaluation to achieve a separation of samples S1 to S20 according to the underlying clinical progression (S1-S10: positive progression; S11-S20: implant failure).

In a second approach, a correlation cluster analysis was carried out from the RPKM numerical values: the Pearson correlation coefficient was calculated for each sample pair (S1-S20) in the genes and plotting was carried out of a so-called "heatmap" of the correlation matrix with the integrated heatmap function. The hypothesis behind this correlation assumes that the calculation yields a sorted list for the 20 clinical results which separates the good results from the clinical failure cases when the relations outlined in the data cited above are statistically significant. The result is shown in FIG. 5. In FIG. 6A, the data for the complete genes with all their exons were compiled. In FIG. 6B, the exons were analyzed individually and independently of the mRNA structure. In other words, alternative splicing is disregarded in FIG. 6A, whereas it is shown in FIG. 6B. It became apparent that the data were sorted corresponding to their origin, with the group S1-10 being separated from the group S11-20. Exceptions are sample S2, which was classified in the transition zone between the two groups, when it was analyzed for genes, and migrated further into the failure group, when it was analyzed for exons, and sample S11, which remained stably in the "wrong" cluster. Altogether, the heatmap yielded a correct "prediction" of the clinical result in 18 of 20 cases, or with a probability of 90%.

The invention claimed is:

1. A method of preparing an implant comprising chondrocytes comprising:
   culturing chondrocytes;
   prognostically assessing prospects of success of an implantation and/or transplantation of the chondrocytes of the implant in vitro by determining mRNA expression in cultured chondrocytes of at least one two-marker combination selected from the group consisting of type II collagen and IL-1 beta; type II collagen and FLT-1; and type II collagen and BSP-2; and
   inoculating the implant with the cultured chondrocytes.

2. The method according to claim 1, wherein the mRNA expression is determined by quantitative real-time PCR.

3. The method of claim 1, wherein the chondrocytes are autologous cells.

4. The method of claim 1, wherein the chondrocytes are articular chondrocytes.

5. The method of claim 1, wherein the chondrocytes are healthy cells.

6. The method of claim 1, wherein the implantation is a support-assisted autologous chondrocyte transplantation.

7. The method of claim 1, wherein the transplantation is an autologous chondrocyte transplantation.

* * * * *

UNITED STATES PATENT AND TRADEMARK OFFICE
CERTIFICATE OF CORRECTION

PATENT NO. : 9,828,636 B2
APPLICATION NO. : 14/779639
DATED : November 28, 2017
INVENTOR(S) : Mollenhauer et al.

It is certified that error appears in the above-identified patent and that said Letters Patent is hereby corrected as shown below:

In the Specification

Column 19, Line 3: after the word "the" insert the following omitted text --probability of such an event was greater when the cartilage defect was classified as degenerative (p = 0.005). However, for patients, the probability of such an event was lower when there was a cartilage defect caused by osteochondritis dissecans (p = 0.04)--.

Signed and Sealed this
Twelfth Day of June, 2018

Andrei Iancu
*Director of the United States Patent and Trademark Office*